(12) United States Patent
Li et al.

(10) Patent No.: US 9,518,923 B1
(45) Date of Patent: Dec. 13, 2016

(54) SYSTEM AND METHODS FOR FLUORESCENCE DETECTION

(71) Applicant: International Business Machines Corporation, Armonk, NY (US)

(72) Inventors: Ning Li, White Plains, NY (US); Devendra K. Sadana, Pleasantville, NY (US); William T. Spratt, Ossining, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/960,667

(22) Filed: Dec. 7, 2015

(51) Int. Cl.
*G01N 21/64* (2006.01)

(52) U.S. Cl.
CPC ........ *G01N 21/645* (2013.01); *G01N 21/6428* (2013.01); *G01N 2021/6463* (2013.01); *G01N 2021/6484* (2013.01); *G01N 2201/061* (2013.01); *G01N 2201/08* (2013.01); *G01N 2201/12* (2013.01)

(58) Field of Classification Search
CPC .............. G01N 21/645; G01N 21/6428; G01N 2021/6484; G01N 2021/12; G01N 2021/08; G01N 2021/061; G01N 2021/6463
See application file for complete search history.

(56) References Cited

U.S. PATENT DOCUMENTS

| | | | |
|---|---|---|---|
| 6,825,921 B1 * | 11/2004 | Modlin | G01N 21/255 235/454 |
| 9,146,235 B2 | 9/2015 | Van Dorpe | |
| 2002/0058273 A1 * | 5/2002 | Shipwash | B01L 3/5027 435/6.12 |
| 2004/0222480 A1 | 11/2004 | Weisbuch | |

(Continued)

FOREIGN PATENT DOCUMENTS

| | | |
|---|---|---|
| CN | 101105455 A | 1/2008 |
| CN | 103245641 A | 8/2013 |

(Continued)

OTHER PUBLICATIONS

CN101105455A Jan. 16, 2008 Machine Translation (8 pages).

(Continued)

*Primary Examiner* — Yara B Green
(74) *Attorney, Agent, or Firm* — Cantor Colburn LLP; Louis Percello

(57) ABSTRACT

A fluorescence detection system is provided. The fluorescence detection system includes a light source adapted to emit excitation light; a sample unit in which a sample is disposed; a first optical fiber adapted to connect the light source to the sample unit; an avalanche photodiode array detector adapted to receive fluorescent light generated by the sample when the sample is irradiated with the excitation light; and a second optical fiber adapted to connect the sample unit to the avalanche photodiode array detector, wherein the second optical fiber has a numerical aperture of equal to or greater than about 0.15 and the second optical fiber is positioned such that a longitudinal axis of the second (Continued)

optical fiber is orthogonal to a longitudinal axis of the first optical fiber. A method for detecting fluorescence and a computer-implemented method for detecting fluorescence are also provided.

19 Claims, 10 Drawing Sheets

(56) References Cited

U.S. PATENT DOCUMENTS

| | | | |
|---|---|---|---|
| 2007/0139652 A1* | 6/2007 | Carpenter, II | G01N 21/6428 |
| | | | 356/417 |
| 2010/0243915 A1 | 9/2010 | Fukuzawa | |
| 2013/0112848 A1* | 5/2013 | Lin | G01J 1/44 |
| | | | 250/206 |

FOREIGN PATENT DOCUMENTS

| | | |
|---|---|---|
| CN | 103344615 A | 10/2013 |
| CN | 103698276 A | 4/2014 |
| CN | 104634905 A | 5/2015 |
| WO | WO2009055012 A2 | 4/2009 |

OTHER PUBLICATIONS

CN103245641B Oct. 29, 2014 Machine Translation (7 pages).
CN103344615B May 20, 2015 Machine Translation (8 pages).
CN103698276A Apr. 2, 2014 Machine Translation (6 pages).
CN104634905A May 20, 2015 Machine Translation (8 pages).

* cited by examiner

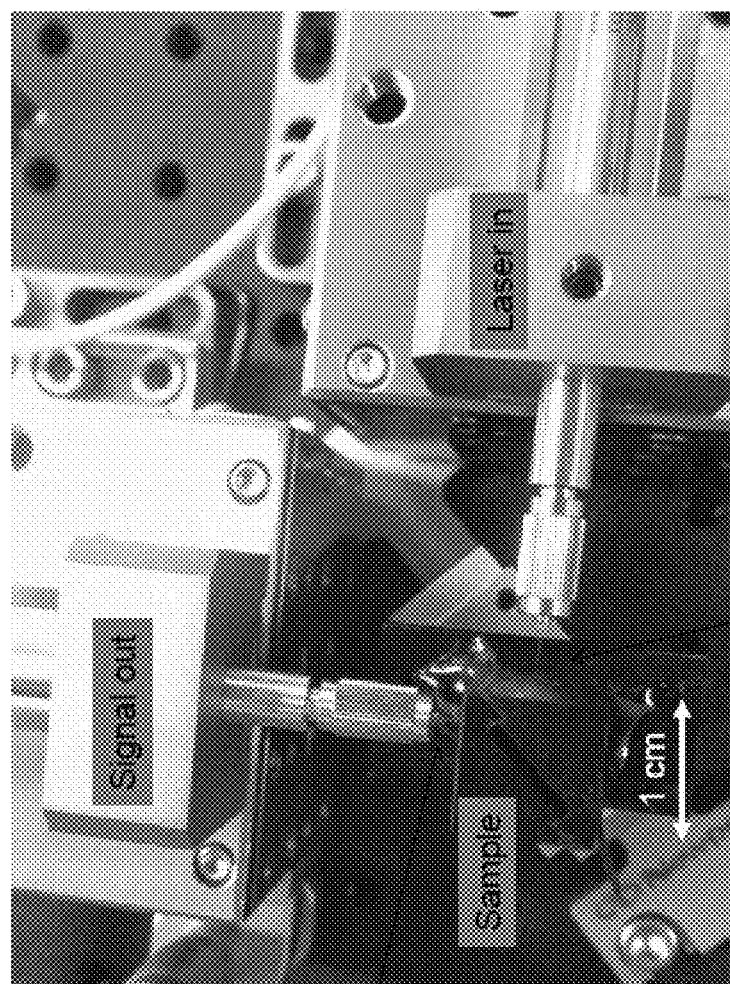

SYSTEM AND METHODS FOR FLUORESCENCE DETECTION

BACKGROUND

The present invention relates to fluorescence detection, and more specifically, to systems and methods for fluorescence detection.

Fluorescent markers are used to label a particular molecule, such as a protein, antibody or amino acid, of interest. Fluorescent detectors are used to quantitatively measure the fluorescence generated by a sample being evaluated. Thus, when the fluorescent detector detects fluorescence, the fluorescent marker, and hence the molecule of interest, is present in the sample being evaluated. Fluorescent detectors may employ numerous components in complex configurations, consume significant amounts of power and/or may be sizeable in shape e.g., laboratory-bench size. Fluorescent detectors also have sample volume and/or concentration detection limits below which fluorescence of samples cannot be detected.

Therefore, a need exists for a fluorescent detection system which addresses one or more of the above drawbacks.

SUMMARY

According to an embodiment of the present invention, a fluorescence detection system comprises a light source adapted to emit excitation light; a sample unit having a sample disposed therein; a first optical fiber adapted to connect the light source to the sample unit; an avalanche photodiode array detector adapted to receive fluorescent light generated by the sample when the sample is irradiated with the excitation light; and a second optical fiber adapted to connect the sample unit to the avalanche photodiode array detector, wherein the second optical fiber has a numerical aperture of equal to or greater than about 0.15 and the second optical fiber is positioned such that a longitudinal axis of the second optical fiber is orthogonal to a longitudinal axis of the first optical fiber.

According to another embodiment of the present invention, a method for detecting fluorescence comprises emitting excitation light from a light source through a first optical fiber to a sample in a sample unit; and receiving, by an avalanche photodiode array detector, through a second optical fiber, fluorescent light generated by the sample when the sample is irradiated with the excitation light; wherein the second optical fiber has a numerical aperture of equal to or greater than about 0.15 and is positioned such that a longitudinal axis of the second optical fiber is orthogonal to a longitudinal axis of the first optical fiber.

According to another embodiment of the present invention, a computer-implemented method for detecting fluorescence comprising emitting, by a processor of a computer system, excitation light from a light source to a sample in a sample unit through a first optical fiber; receiving, by an avalanche photodiode array detector, through a second optical fiber, fluorescent light generated by the sample when the sample is irradiated with the excitation light, wherein the second optical fiber has a numerical aperture of equal to or greater than about 0.15 and is positioned such that a longitudinal axis of the second optical fiber is orthogonal to a longitudinal axis of the first optical fiber; receiving, by the processor of the computer system, sample information from the avalanche photodiode array detector; and storing, by the processor of the computer system, the sample information in a memory.

BRIEF DESCRIPTION OF THE DRAWINGS

The accompanying figures wherein reference numerals refer to identical or functionally similar elements throughout the separate views, and which together with the detailed description below are incorporated in and form part of the specification, serve to further illustrate various embodiments and to explain various principles and advantages all in accordance with the present invention, in which:

FIG. 2 is a photograph of an embodiment of the fluorescence detection system;

DETAILED DESCRIPTION

Figure 1A:
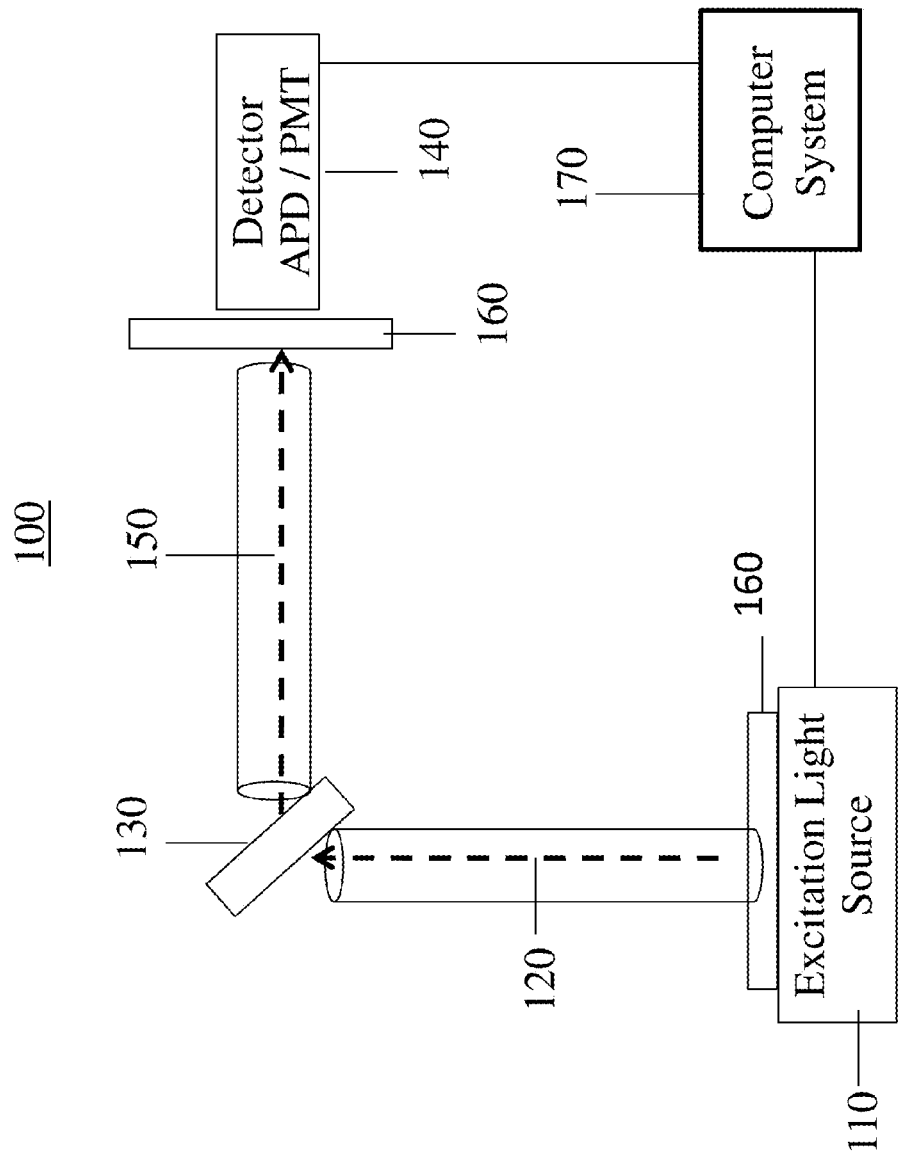
FIG. 1A is a functional diagram of an embodiment of the fluorescence detection system.

With reference now to FIG. 1A, a functional diagram of an embodiment of the fluorescence detection system is shown. The fluorescence detection system 100 includes a light source 110 adapted to emit excitation light. A first optical fiber 120 is adapted to connect the light source 110 to a sample unit 130 having a sample disposed therein (not shown). An avalanche photodiode array detector 140 is adapted to receive fluorescent light generated by the sample when the sample is irradiated with the excitation light. A second optical fiber 150 is adapted to connect the sample unit 130 to the avalanche photodiode array ("APD") array detector 140. The second optical fiber 150 is positioned such that a longitudinal axis of the second optical fiber 150 is orthogonal to a longitudinal axis of the first optical fiber 120.

One or more optional filters 160 may be employed in the fluorescence detection system 100. Any filter suitable for use in a fluorescence detection system may be employed. In an embodiment, the one or more filters 160 comprise a dielectric filter, an absorptive filter, a fiber grating-based filter or a combination comprising at least one of the foregoing filters. In an embodiment, a filter 160 is disposed between the light source 110 and the first optical fiber 120. In another embodiment, a filter 160 is disposed between the second optical fiber 150 and the APD array detector 140.

In an embodiment, the fluorescence detection system 100 further comprises a computer system 170 having a memory (not shown), and a processor (not shown) communicatively coupled to the memory, the light source 110 and the APD array detector 140. The processor is configured to activate the light source 110 to emit excitation light; receive sample information from the APD array detector 140; and store the sample information in the memory.

In an embodiment, the processor of the computer system 170 is further configured to select a mode of operation for the APD array detector 140. In an aspect of the embodiment, the processor is configured to select a photon-counting mode of photon detection for the APD array detector 140. In another aspect of the embodiment, the processor is configured to select a linear photomultiplier mode of photon detection for the APD array detector 140.

In an embodiment, the second optical fiber 150 has a numerical aperture of equal to or greater than about 0.15. In another embodiment, the second optical fiber 150 has a numerical aperture of equal to or greater than about 0.20. In still another embodiment, the second optical fiber 150 has a numerical aperture of equal to or greater than about 0.25. In yet another embodiment, the second optical fiber 150 has a numerical aperture of equal to or greater than about 0.30.

The sample unit 130 may be of any shape and/or material suitable to hold the sample in a position for detection by the APD array detector 140. In an embodiment, the sample unit 130 is a static sample unit, e.g., a cuvette. In another embodiment, the sample unit 130 is a dynamic sample unit, e.g., microfluidic channel.

The sample unit 130 may accommodate samples of varying volumes, including relatively small volumes. In an embodiment, the sample unit 130 has a volume capacity of less than or equal to about one cubic centimeter. In an embodiment, a volume of a sample in the sample unit 130 is equal to or less than about 100 nanoliters. In another embodiment, a volume of a sample in the sample unit 130 is equal to or less than about 50 nanoliters. In another embodiment, a volume of a sample in the sample unit 130 is equal to or less than about 40 nanoliters. In still another embodiment, a volume of a sample in the sample unit 130 is from about 30 nanoliters to about 100 nanoliters, specifically about 32 nanoliters to about 50 nanoliters, more specifically about 35 nanoliters to about 40 nanoliters, and even more specifically about 38 nanoliters.

The APD array detector 140 receives and detects fluorescent light generated by the sample in the sample unit 130. Avalanche photodiodes are photodiodes that can generate a relatively large electrical current signal in response to the receipt of a relatively low-power optical signal. The APD array detector 140 thus has high responsivity. In an embodiment, the APD array detector 140 is configured to selectively switch between a photon-counting mode for relatively lower concentrations and a linear photomultiplier mode of photon detection mode for relatively higher concentrations.

The configuration of the fluorescence detection system 100 is also very compact in comparison to bench-size fluorescence detection systems. In an embodiment, the fluorescence detection system 100 is portable. In another embodiment, the fluorescence detection system 100 is battery-powered. The fluorescence detection system 100 employs a reduced number of system elements in comparison to other fluorescence detection systems. In an embodiment, the fluorescence detection system 100 is filterless. In another embodiment, the fluorescence detection system 100 is lens-free.

Figure 1B:
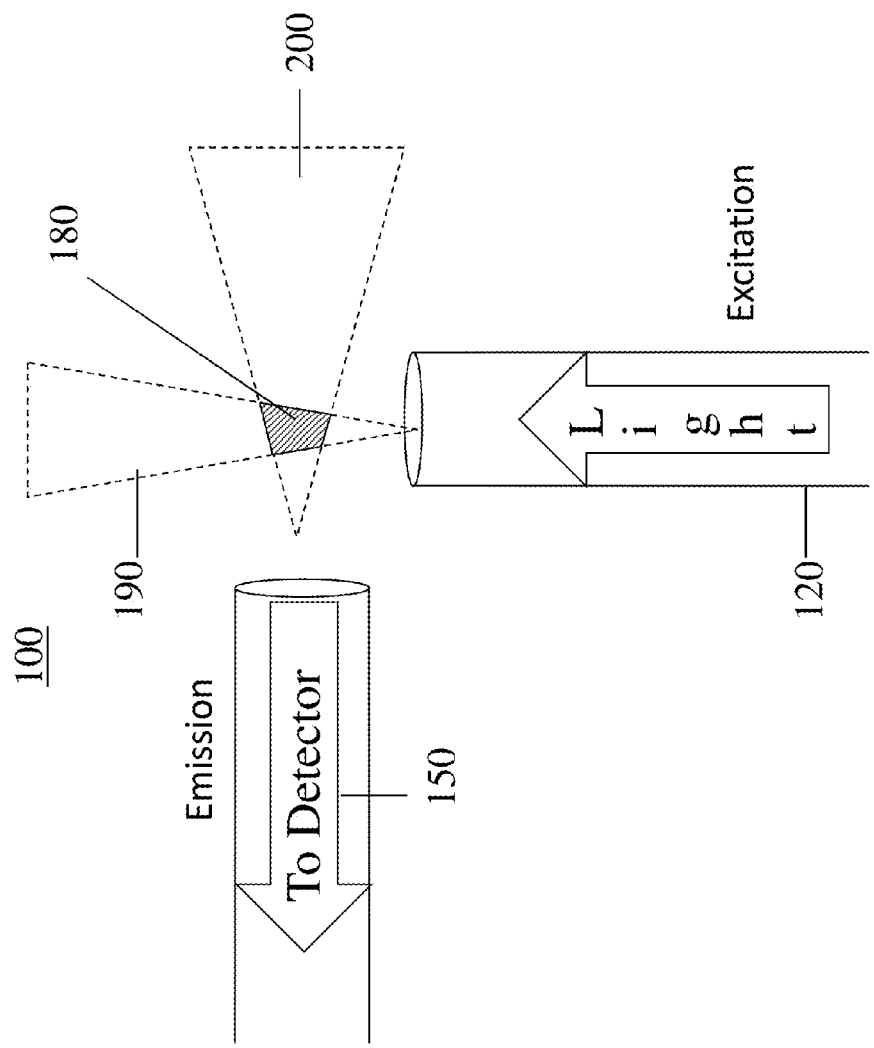
FIG. 1B is a functional diagram of the sample volume in the embodiment of the fluorescence detection system in FIG. 1A.

The orthogonal configuration of the first optical fiber 120 and the second optical fiber 150, the relatively high numerical aperture of the second fiber 150 and the APD array detector 140 allow for samples having relatively small volumes and/or concentrations of fluorescent markers to be detected by the fluorescence detection system 100. Referring to FIG. 1B, a functional diagram of the sample volume in the embodiment of the fluorescence detection system in FIG. 1A is shown. The volume of a sample 180 in the sample unit (not shown) irradiated with excitation light from the light source 110 and detected by the APD array detector 140 is shown as the space in which an excitation light cone 190 and fluorescence emission cone 200 overlap. The orthogonal configuration of the first optical fiber 120 and the second optical fiber 150 reduce the collection of scattered excitation light and/or stray light, thereby reducing background signal in the APD array detector 140, and facilitates detection of fluorescence in a relatively small volume of the sample 180. In an embodiment, the excitation light cone 190, or volume, the fluorescence emission cone 200, or volume, and/or amount of light emitted by the light source are adjusted as desired by varying the optical fibers employed as the first optical fiber 120 and/or the second optical fiber 150.

The fluorescence detection system 100 has high-sensitivity relative to other fluorescence detection systems. In an embodiment, the fluorescence detection system 100 has a fluorescence detection limit of equal to or greater than about one fluorescent particle per microliter for fluorescent particles having an average diameter of about two micrometers. In another embodiment, the fluorescence detection system 100 has a fluorescence detection limit of equal to or greater than about 100 fluorescent particles per microliter for fluorescent particles having an average diameter of about 50 nanometers.

Referring to FIG. 2, a photograph of an embodiment of the fluorescence detection system 200 is shown. The elements of the fluorescence detection system 200 are the same as those described above for the fluorescence detection system 100 shown in FIG. 1. As may be seen from the photograph of the fluorescence detection system 200, the first optical fiber connecting the laser light source to the sample unit is adjacent to the light source at one end and the sample unit at the other end. The end of the first optical fiber adjacent to the sample unit forms an interface 210 between the first optical fiber and the sample unit. As may also be seen from the photograph of the fluorescence detection system 200, the second optical fiber connecting the sample unit to the APD array detector is adjacent to the sample unit at one end and the APD array detector at the other end. The end of the second optical fiber adjacent to the APD array detector forms an interface 220 between the first optical fiber and the sample unit.

In an embodiment, one or both ends of the first optical fiber are not tapered. In another embodiment, one or both ends of the second optical fiber are not tapered. In still another embodiment, one or both ends of the first optical fiber are not tapered and one or both ends of the second optical fiber are not tapered.

Figure 3A:
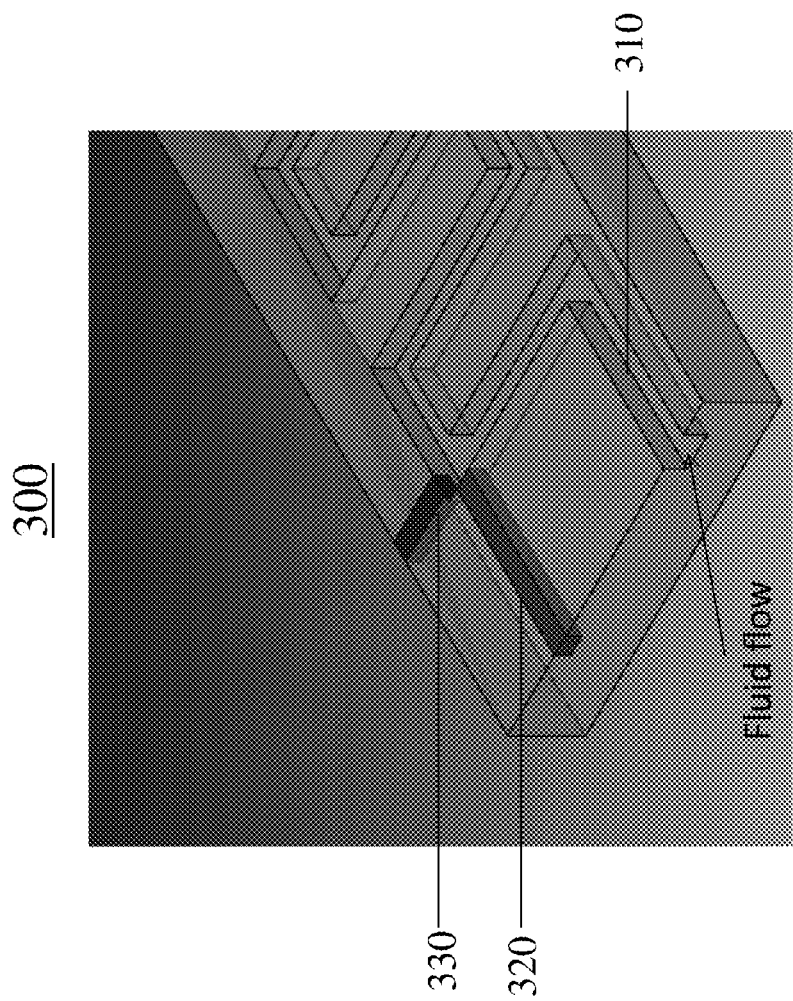
FIG. 3A is a schematic diagram of an embodiment of the fluorescence detection system using a microfluidic chip.

Referring to FIG. 3A, a schematic diagram of an embodiment of the fluorescence detection system integrated into a microfluidic chip 300 is shown. The microfluidic chip 300 includes a microfluidic channel 310 through which a sample fluid flows. The first optical fiber (or "waveguide") 320 is disposed in a position orthogonal to the second optical fiber (or "waveguide") 330. The remaining features of the fluorescence detection system 200 are the same as those described above with regard to FIG. 1.

Figure 3B:
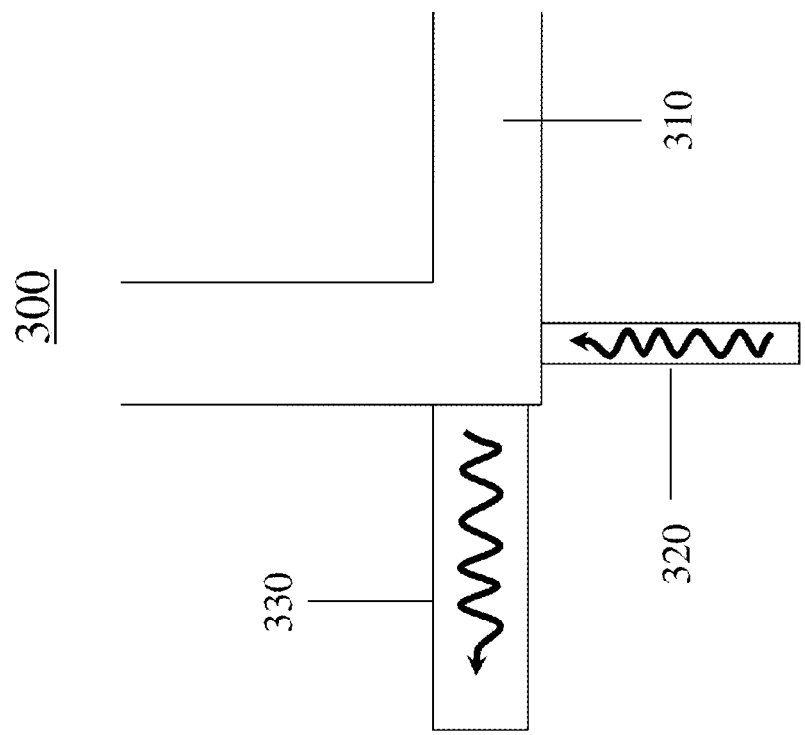
FIG. 3B is a functional diagram of a portion of the microfluidic chip in FIG. 5.

Referring to FIG. 3B, a functional diagram of a portion of the microfluidic chip 300 of FIG. 3A is shown. The first optical fiber 320 transmits excitation light from a light source (not shown) to a sample in the microfluidic channel 310. The second optical fiber 330 emits fluorescent light generated from the sample to an array APD array detector (not shown).

In an embodiment, a method for detecting fluorescence comprises emitting excitation light from a light source through a first optical fiber to a sample in a sample unit; and receiving, by an avalanche photodiode array detector, through a second optical fiber, fluorescent light generated by the sample when the sample is irradiated with the excitation light; wherein the second optical fiber has a numerical aperture of equal to or greater than about 0.15 and is positioned such that a longitudinal axis of the second optical fiber is orthogonal to a longitudinal axis of the first optical fiber.

In another embodiment, a computer-implemented method for detecting fluorescence comprises emitting, by a processor of a computer system, excitation light from a light source to a sample in a sample unit through a first optical fiber; receiving, by an avalanche photodiode array detector, through a second optical fiber, fluorescent light generated by the sample when the sample is irradiated with the excitation light, wherein the second optical fiber has a numerical aperture of equal to or greater than about 0.15 and is positioned such that a longitudinal axis of the second optical fiber is orthogonal to a longitudinal axis of the first optical fiber; receiving, by the processor of the computer system, sample information from the avalanche photodiode array detector; and storing, by the processor of the computer system, the sample information in a memory.

Figure 4:
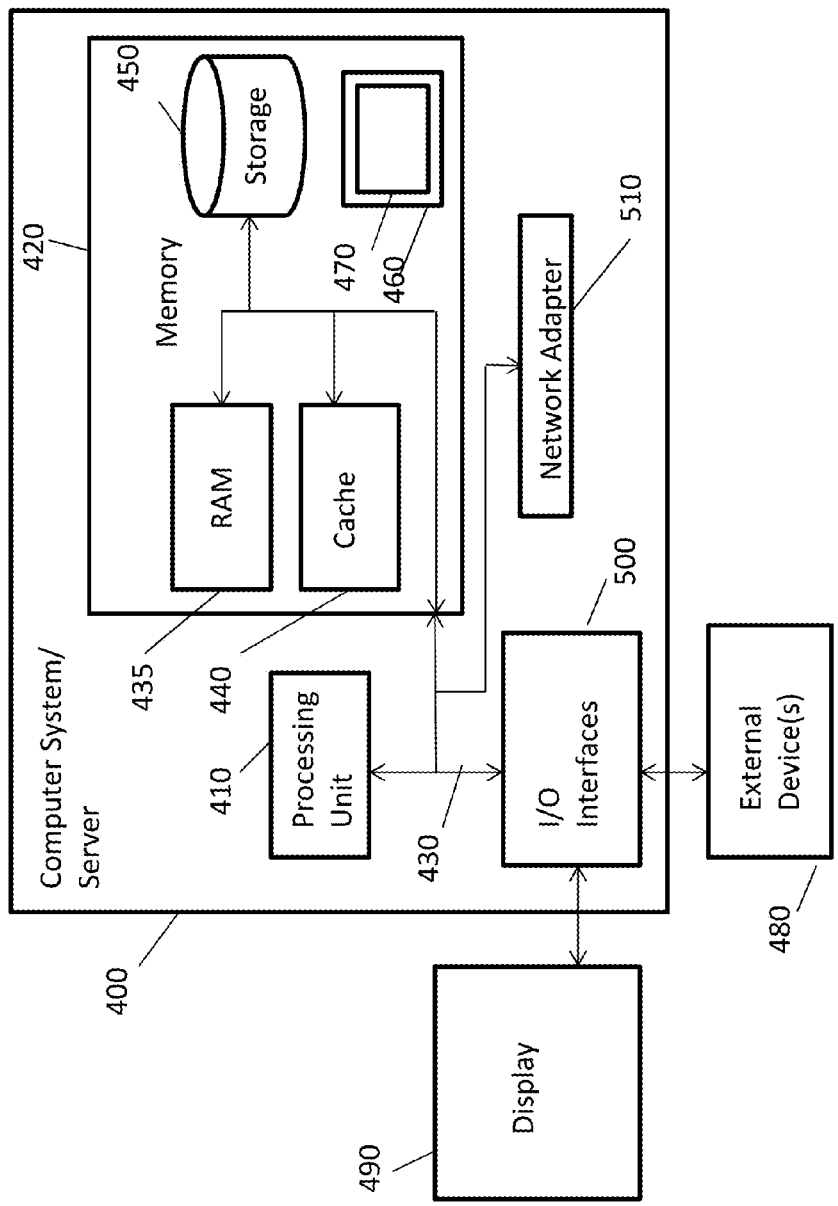
FIG. 4 is a block diagram illustrating an embodiment of an information processing system.

Referring to FIG. 4, a block diagram illustrating an information processing system is shown. The information processing system 400 is based upon a suitably configured processing system configured to implement one or more embodiments described herein. Any suitably configured processing system can be used as the information processing system 400 in the embodiments described herein. The components of the information processing system 400 can include, but are not limited to, one or more processors or processing units 410, a system memory 420 and a bus 430 that couples various system components including the system memory 420 to the processor 410.

The bus 430 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture bus, Micro Channel Architecture bus, Enhanced ISA bus, Video Electronics Standards Association local bus and Peripheral Component Interconnects bus.

The system memory 420 can also include computer system readable media in the form of volatile memory, such as random access memory ("RAM") 435 and/or cache memory 440. The information processing system 400 can further include other removable/non-removable, volatile/non-volatile computer system storage media. By way of example only, a storage system 450 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 430 by one or more data media interfaces. The memory 420 can include at least one program product having a set of program modules that are configured to carry out the functions of the embodiment described herein.

Program/utility 460, having a set of program modules 470, may be stored in memory 420 by way of example, and not limitation, as well as an operating system, one or more application programs, other program modules, and program data. Each of the operating system, one or more application programs, other program modules, and program data or some combination thereof, may include an implementation of a networking environment. Program modules 470 generally carry out the functions and/or methodologies of the embodiments described herein.

The information processing system 400 can also communicate with one or more external devices 480 such as a keyboard, a pointing device, a display 490, etc.; one or more devices that enable a user to interact with the information processing system 400; and/or any devices, e.g., network card, modem, etc., that enable computer system/server 400 to communicate with one or more other computing devices. Such communication can occur via I/O interfaces 500. Still yet, the information processing system 400 can communicate with one or more networks such as a local area network, a general wide area network, and/or a public network, e.g., the Internet, via network adapter 510. As depicted, the network adapter 510 communicates with the other components of information processing system 400 via the bus 430. Other hardware and/or software components can also be used in conjunction with the information processing system 400. Examples include, but are not limited to: microcode, device drivers, redundant processing units, external disk drive arrays, RAID systems, tape drives and data archival storage systems.

Certain aspects of the embodiments described herein may be a system, method or computer program product. Accordingly, the embodiments described herein may take the form of an entirely hardware embodiment, an entirely software embodiment (including firmware, resident software, microcode, etc.) or an embodiment combining software and hardware aspects that may all generally be referred to herein as a "circuit," "module" or "system." Furthermore, embodiments described herein may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory, a read-only memory, an erasable programmable read-only memory, an optical fiber, a portable compact disc read-only memory, an optical storage device, a magnetic storage device, or any suitable combination of the foregoing. In the context of this document, a computer readable storage medium may be any tangible medium that can contain, or store a program for use by or in connection with an instruction execution system, apparatus or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for the embodiments described herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been discussed above with reference to flowchart illustrations and/or block diagrams of methods, apparatus (systems) and computer program products according to various embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 5:
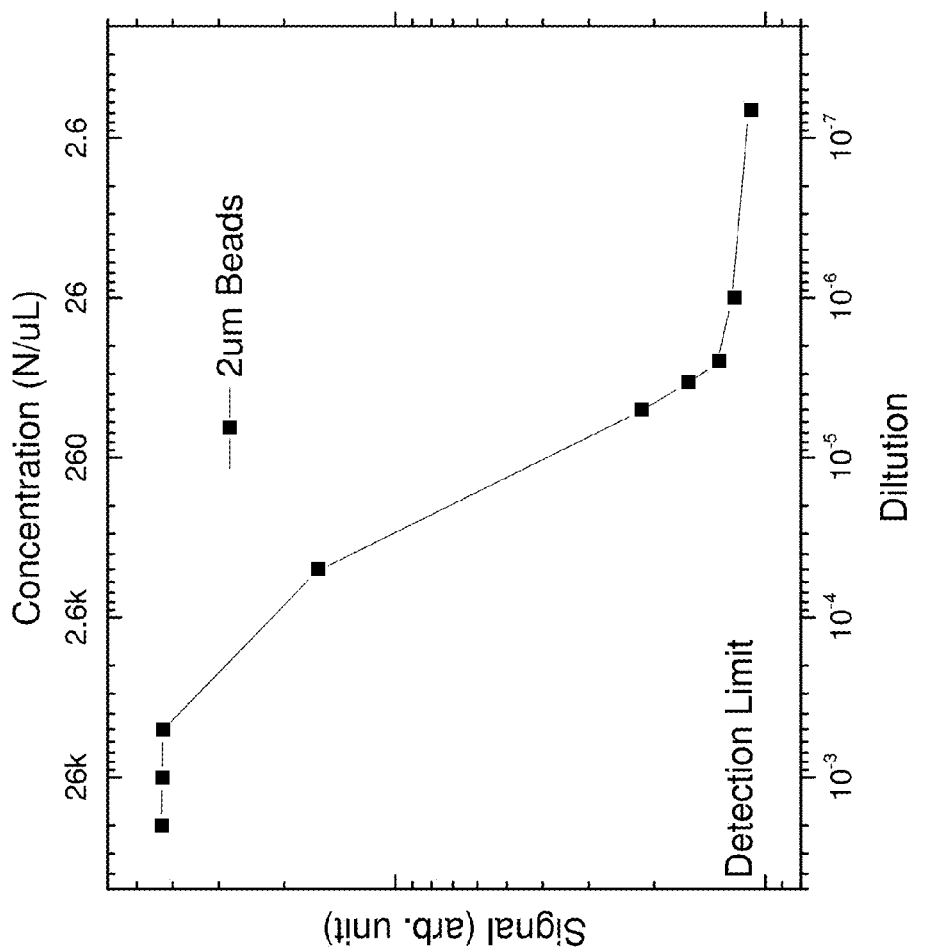
FIG. 5 is a graph of a concentration and dilution of a sample against signal intensity using fluorescent sphere-shaped particles having an average diameter of 2 micrometers.

The following examples were conducted to demonstrate the high-sensitivity of the fluorescence detection system. Referring to FIG. 5, a graph of a concentration in number of fluorescent particles N per microliter (N/µL) and dilution of a sample against signal intensity in arbitrary units using fluorescent sphere-shaped particles having an average diameter of 2 micrometers is shown. As may be seen from the graph in FIG. 5, fluorescence was detected at a concentration level as low as 2.6 N/µL, and even as low as about 1.0 N/µL.

Figure 6:
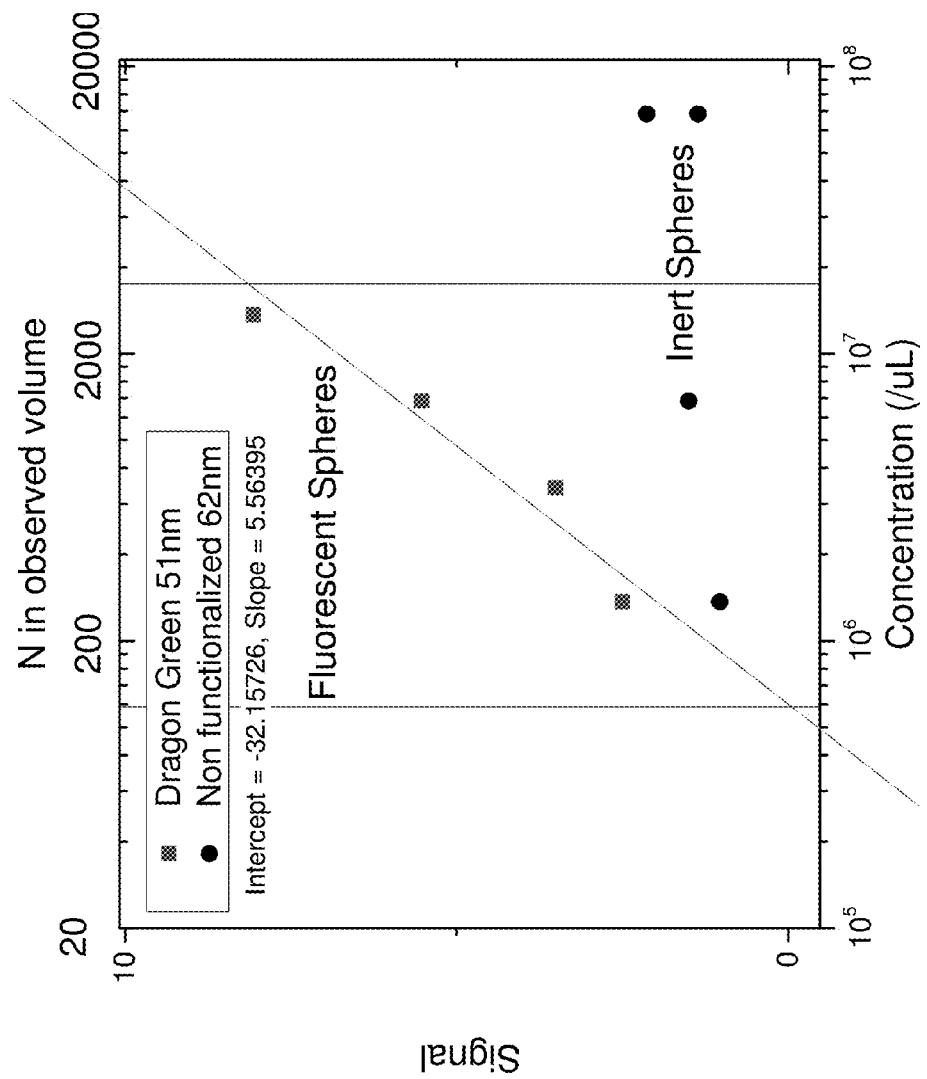
FIG. 6 is a graph of a volume and concentration of a sample against signal intensity using fluorescent sphere-shaped particles having an average diameter of 50 nanometers.

Referring to FIG. 6, a graph of a volume and concentration of a sample against signal intensity using fluorescent spheres having an average diameter of 50 nanometers is shown. The same conditions and parameters described above with regard to FIG. 5 were employed in this experiment, except that fluorescent sphere-shaped particles having an average diameter of 50 nanometers were used instead of fluorescent sphere-shaped particles having an average diameter of 2 micrometers. As may be seen from the graph in FIG. 5, fluorescence of the significantly smaller fluorescent sphere-shaped particles was detected at a concentration level as low as 200 N/µL, and even at concentrations below 200 N/µL.

Figure 7:
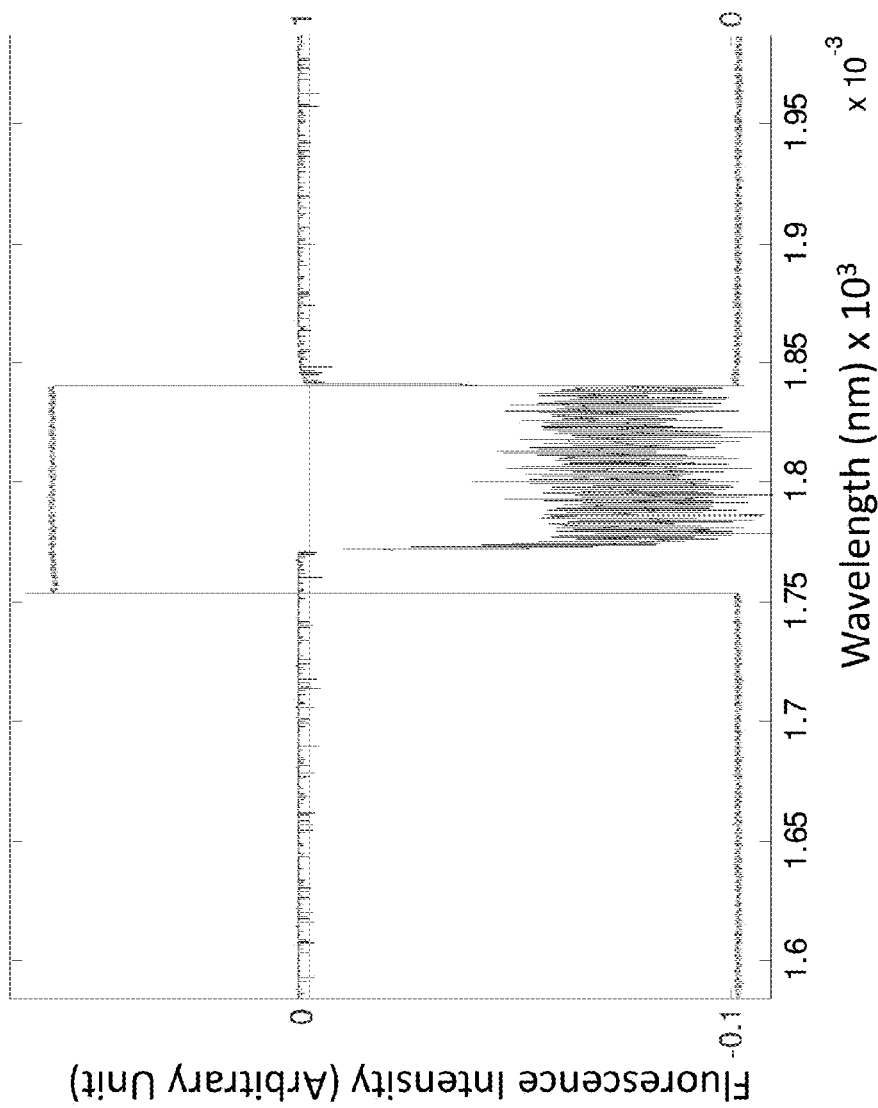
FIG. 7 is a graph showing the fluorescence detection system in a linear mode.

Referring to FIG. 7, a graph showing the APD array detector in the fluorescence detection system in a linear mode is shown. As may be seen from FIG. 7, the linear mode uses as integrated multi-photon signal to detect fluorescence in a sample having a relatively high concentration of $5 \times 10^6$/milliliter (500:1).

Figure 8:
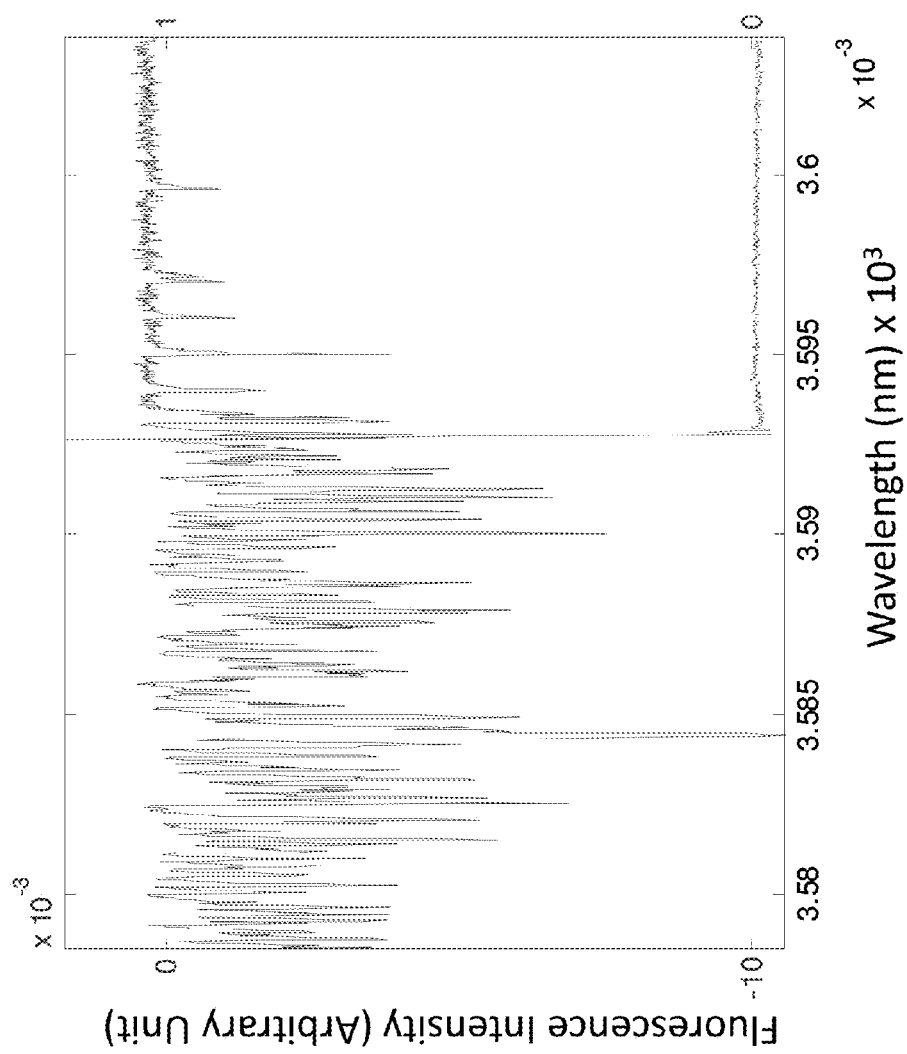
FIG. 8 is a graph showing the fluorescence detection system in a photon counting mode.

Referring to FIG. 8, is a graph showing the fluorescence detection system in a photon counting mode is shown. As may be seen from FIG. 8, the photon counting mode uses a single photon signal to detect fluorescence in a sample having a relatively low concentration of fluorescent sphere-shaped particles of $1 \times 10^5$/milliliter (20K:1).

The flowchart and block diagrams in the Figures illustrate the architecture, functionality and operation of possible implementations of systems, methods and computer program products according to various embodiments of the present invention. In this regard, each block in the flowchart or block diagrams may represent a module, segment or portion of instructions which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

What is claimed is:

1. A fluorescence detection system comprising:
a light source adapted to emit excitation light;
a sample unit having a sample disposed therein;
a first optical fiber adapted to connect the light source to the sample unit;
an avalanche photodiode array detector adapted to receive fluorescent light generated by the sample when the sample is irradiated with the excitation light; and
a second optical fiber adapted to connect the sample unit to the avalanche photodiode array detector,
wherein the second optical fiber has a numerical aperture of equal to or greater than about 0.15 and the second optical fiber is positioned such that a longitudinal axis of the second optical fiber is orthogonal to a longitudinal axis of the first optical fiber; and
wherein the fluorescence detection system has a fluorescence detection limit of equal to or greater than about one fluorescent particle per microliter for fluorescent particles having an average diameter of about two micrometers.

2. The fluorescence detection system of claim 1, further comprising:
a memory;
a processor of a computer system communicatively coupled to the memory, the light source and the avalanche photodiode array detector, where the processor is configured to:
activate the light source to emit excitation light;
receive sample information from the avalanche photodiode array detector; and
store the sample information in the memory.

3. The fluorescence detection system of claim 2, wherein the processor is further configured to select a mode of operation for the avalanche photodiode array detector.

4. The fluorescence detection system of claim 3, wherein the processor is configured to select a photon-counting mode of photon detection for the avalanche photodiode array detector.

5. The fluorescence detection system of claim 3, wherein the processor is configured to select a linear photomultiplier mode of photon detection for the avalanche photodiode array detector.

6. The fluorescence detection system of claim 1, wherein a volume of a sample in the sample unit is equal to or less than about 100 nanoliters.

7. The fluorescence detection system of claim 1, wherein a volume of a sample in the sample unit is equal to or less than about 50 nanoliters.

8. The fluorescence detection system of claim 1, wherein the fluorescence detection system has a fluorescence detection limit of equal to or greater than about 100 fluorescent particles per microliter for fluorescent particles having an average diameter of about 50 nanometers.

9. The fluorescence detection system of claim 1, wherein the second optical fiber has a numerical aperture of equal to or greater than about 0.20.

10. The fluorescence detection system of claim 1, wherein the second optical fiber has a numerical aperture of equal to or greater than about 0.25.

11. The fluorescence detection system of claim 1, wherein a volume capacity of the sample unit is less than or equal to about one cubic centimeter.

12. The fluorescence detection system of claim 1, wherein the sample unit is a static sample unit or a dynamic sample unit.

13. The fluorescence detection system of claim 1, wherein the fluorescence detection system further comprises a filter disposed between the light source and the first optical fiber.

14. The fluorescence detection system of claim 1, wherein the fluorescence detection system further comprises a filter disposed between the second optical fiber and the avalanche photodiode array detector.

15. The fluorescence detection system of claim 1, wherein the fluorescence detection system is lens-free.

16. A method for detecting fluorescence comprising:
emitting excitation light from a light source through a first optical fiber to a sample in a sample unit; and
receiving, by a avalanche photodiode array detector, through a second optical fiber, fluorescent light generated by the sample when the sample is irradiated with the excitation light;
wherein the second optical fiber has a numerical aperture of equal to or greater than about 0.15 and is positioned such that a longitudinal axis of the second optical fiber is orthogonal to a longitudinal axis of the first optical fiber; and
wherein the fluorescence detection system has a fluorescence detection limit of equal to or greater than about one fluorescent particle per microliter for fluorescent particles having an average diameter of about two micrometers.

17. The method of claim 16, further comprising selecting a mode of photo detection for the avalanche photodiode array detector.

18. A computer-implemented method for detecting fluorescence comprising:
emitting, by a processor of a computer system, excitation light from a light source to a sample in a sample unit through a first optical fiber;
receiving, by an avalanche photodiode array detector, through a second optical fiber, fluorescent light generated by the sample when the sample is irradiated with the excitation light, wherein the second optical fiber has a numerical aperture of equal to or greater than about 0.15 and is positioned such that a longitudinal axis of the second optical fiber is orthogonal to a longitudinal axis of the first optical fiber, and wherein the avalanche photodiode array detector has a fluorescence detection limit of equal to or greater than about one fluorescent particle per microliter for fluorescent particles having an average diameter of about two micrometers;
receiving, by the processor of the computer system, sample information from the avalanche photodiode array detector; and
storing, by the processor of the computer system, the sample information in a memory.

19. The method of claim 18, further comprising selecting a mode of photo detection for the avalanche photodiode array detector.

* * * * *